(12) United States Patent
Termanini

(10) Patent No.: US 9,056,020 B1
(45) Date of Patent: Jun. 16, 2015

(54) ACETABULAR CUP DEVICE AND METHOD THEREOF

(71) Applicant: Zafer Termanini, Port Saint Lucie, FL (US)

(72) Inventor: Zafer Termanini, Port Saint Lucie, FL (US)

(*) Notice: Subject to any disclaimer, the term of this patent is extended or adjusted under 35 U.S.C. 154(b) by 0 days.

(21) Appl. No.: 14/326,006

(22) Filed: Jul. 8, 2014

(51) Int. Cl.
*A61B 17/58* (2006.01)
*A61B 17/60* (2006.01)
*A61F 2/00* (2006.01)
*A61F 2/46* (2006.01)

(52) U.S. Cl.
CPC .................................. *A61F 2/4609* (2013.01)

(58) Field of Classification Search
USPC .......................................................... 606/99
See application file for complete search history.

(56) References Cited

U.S. PATENT DOCUMENTS 8,764,758 B2 * 7/2014 Echeverri ........................ 606/88

* cited by examiner

*Primary Examiner* — Sameh Boles
(74) *Attorney, Agent, or Firm* — Samir Termanini

(57) ABSTRACT

Positioning an acetabular cup in a desired optimal alignment in relation to the patient's pelvis using conventional fluoroscopic equipment readily available in operating rooms in conjunction with a metallic jig as guide. The device having inclination metallic rods at 45 degrees angle to the cup impactor and anteversion rod situated at a distance from the midline that correspond to the degree of inclination. When said inclination and anteversion shafts are aligned with central anatomical structures such as symphysis pubis and middle of first sacral vertebra will result in correct placement of the acetabular cup at the desired version.

8 Claims, 5 Drawing Sheets

ACETABULAR CUP DEVICE AND METHOD THEREOF

FIELD OF THE INVENTION

The present invention relates to an orthopedic device and more particularly to a device used for precise acetabular cup positioning during hip surgery.

BACKGROUND OF THE INVENTION

During total hip replacement surgery, placement of the acetabular cup is primordial. The accurate position of the acetabular cup is critical for good functioning of the implant resulting in successful clinical outcome. Malpositioning if the acetabular cup will lead to significant complications resulting in increased risk of dislocation, premature wear of the bearing surfaces and release of polyethylene debris and particles that will result in osteolysis and acetabular component loosening. Impingement is a major source of loosening and metallosis, where metallic debris lead to severe local tumor like inflammatory reactions. This will ultimately lead to extensive revisions of the implants.

Acetabular cup orientation is defined by the inclination and anteversion of the equatorial plane of said cup vis-à-vis the cardinal coronal and sagittal planes passing vertically through the center of the pelvis. Optimal orientation of the cup will prevent dislocation, increase range of motion and reduce edge loading and impingement. Postoperative radiographs measurements have shown that 50% of the cups inserted by experienced surgeons were outside the desired "safe zone" of Lewinneck, defined as a cup placed at 45 degrees of inclination and 15 degrees of anteversion The problem with the conventional methods of orienting the acetabular cup during total hip surgery is that they rely on the position of patient during the surgical procedure notwithstanding the fact that the position of the pelvis while patient is covered under surgical drapes may not be accurately flat but rotated or tilted. Therefore, relying on the position of the patient may lead to significant inaccuracy of the final inclination and the anteversion of the implanted acetabular cup. At times, surgeons use inclination devises attached to cup inserter and pointed in the direction of the patient's shoulder. Again, the position of the patient under the surgical drapes may be rotated and not completely supine or flat leading to malposition of the implanted cup. More invasive techniques have been in use recently including computerized navigation. However, these devices require invasive insertion of probes into anatomical references such as the iliac crest and other anatomical pelvic landmarks such as the anterior iliac spines. The use of these probes requires separate skin incisions leading and subsequent local skin irritations. Furthermore, navigation devices require expensive monitoring devices and assigned and specially trained technicians to register the specifically designated landmarks. Said registration can be lengthy and time consuming requiring sophisticated monitoring devices and equipment.

SUMMARY OF THE INVENTION

Described herein is an intraoperative guidance device for the insertion and accurate acetabular cup orienting during hip surgery, the device comprising a primary vertical shaft having a first end configured to be firmly coupled orthogonally to the acetabular cup inserter and a second end attached to a secondary horizontal shaft that is slidably attached to said primary shaft at a fixed orthogonal angle. An elbow connector with locking nuts assures fixation of both shafts and prevent further sliding. Two inclination alignment metallic rods are horizontally superimposed in a parallel fashion to each other and connected by a connecting cylinder. The secondary horizontal shaft slidably transfixes said central bar through a channel situated between the two inclination rods. Said channel forms a 45 degrees angle with the two parallel bars.

The present invention describes a method for accurately positioning the acetabular cup during implantation. It utilizes X-rays fluoroscopy with image intensification that is readily available in every operating room and routinely used during total hip replacement surgery. It is to be noted that surgeons currently use x-rays to estimate the position of the acetabular cup during insertion. However, it remains a simple estimate since it is not correlated with true pelvic orientation or tilt. The inclination of 45 degrees is usually estimated, however, the anteversion estimation remains inaccurate unless it is correctly correlated with a fixed anatomical reference or landmarks of the pelvis such as the first sacral vertebrae (promontoire) and the symphysis pubis. Said landmarks are centrally located in the midline along a sagittal central plane. The position of the pelvis under the surgical drapes may not be flat or true supine and may be rotated or tilted. The patient may not be lying in a truly supine position and may have rotated or tilted to one side or the other during reaming process. The spatial relationship between the acetabular cavity, sacrum and symphysis pubis remain the same vis-à-vis to the central sagittal plane, regardless of the position of the patient while laying down on the operating table.

The device of this invention will provide an accurate spatial and geometrical relation between the above-mentioned anatomical landmarks and the true position of the acetabular cup-inserting device regardless the tilt or malposition of the patient, using conventional C-arm X-rays fluoroscopy. When the radiological shadow of the two anteversion parallel rods is placed over the midline of the pelvis aligned and superimposed under fluoroscopy, the device will automatically place the cup inserter into a 45 degrees inclination and neutral anteversion. This may require the surgeon to manipulate and slide the horizontal shaft so that the shadow of the two rods become on and superimposed on the midline anatomical structures. Once the inclination is established, the operating surgeon will apply the desired anteversion degree by sliding the anteversion bracket onto the sliding numeric anteversion scale visibly printed onto the horizontal secondary shaft then lock it securely into position by tightening locking knob. Subsequently, the operating surgeon will remove the upper metallic inclination rod and slid it into the channel located into the anteversion bracket. In order to maintain and secure the already established 45 degrees inclination, the anteversion channel also forms 45 degrees angle with the lower inclination bar.

Subsequent to the above steps, the operating surgeon will establish the proper anteversion by raising and tilting the inserter to the predetermined anteversion and align, under fluoroscopy, the anteversion rod with the lower inclination rod and superimpose them with the midline pelvic anatomical structures. The anteversion process, as described, may displace the lower alignment rod beyond the midline structures under X-rays, so the operating surgeon may have to release the locking mechanism of the secondary shaft and slide it back to the midline so that the lower inclination rod coincide with the center of the pelvis.

BRIEF DESCRIPTION OF THE DRAWINGS

Various other objects, features and attendant advantages of the present invention will become fully appreciated as the same become better understood when considered in conjunction with the accompanying drawings, in which the same reference number is used throughout the several views to refer to an identical or similar, wherein.

DETAILED DESCRIPTION OF THE INVENTION

Figure 1:
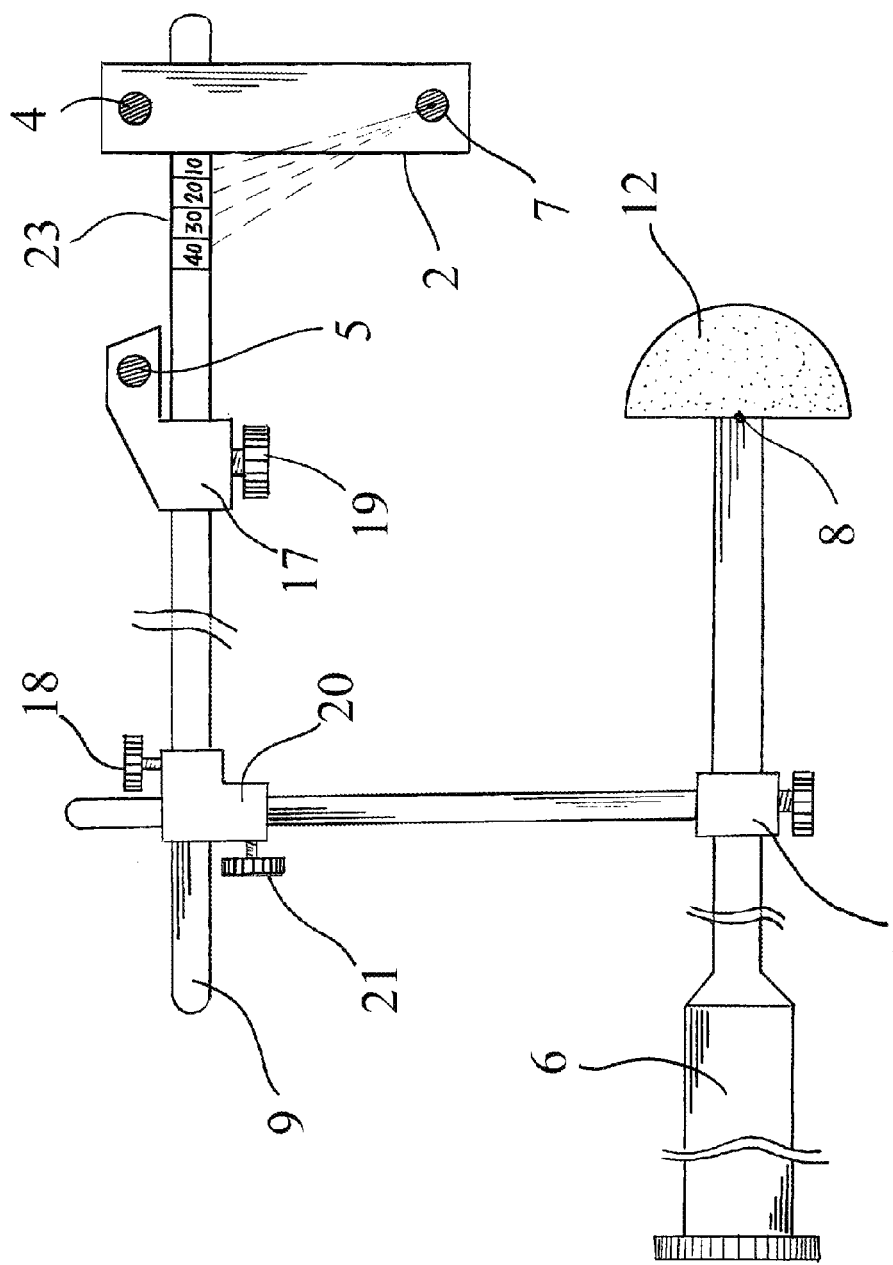
FIG. 1 is a perspective side view of the cup positioning device and its attachments.
Figure 2:
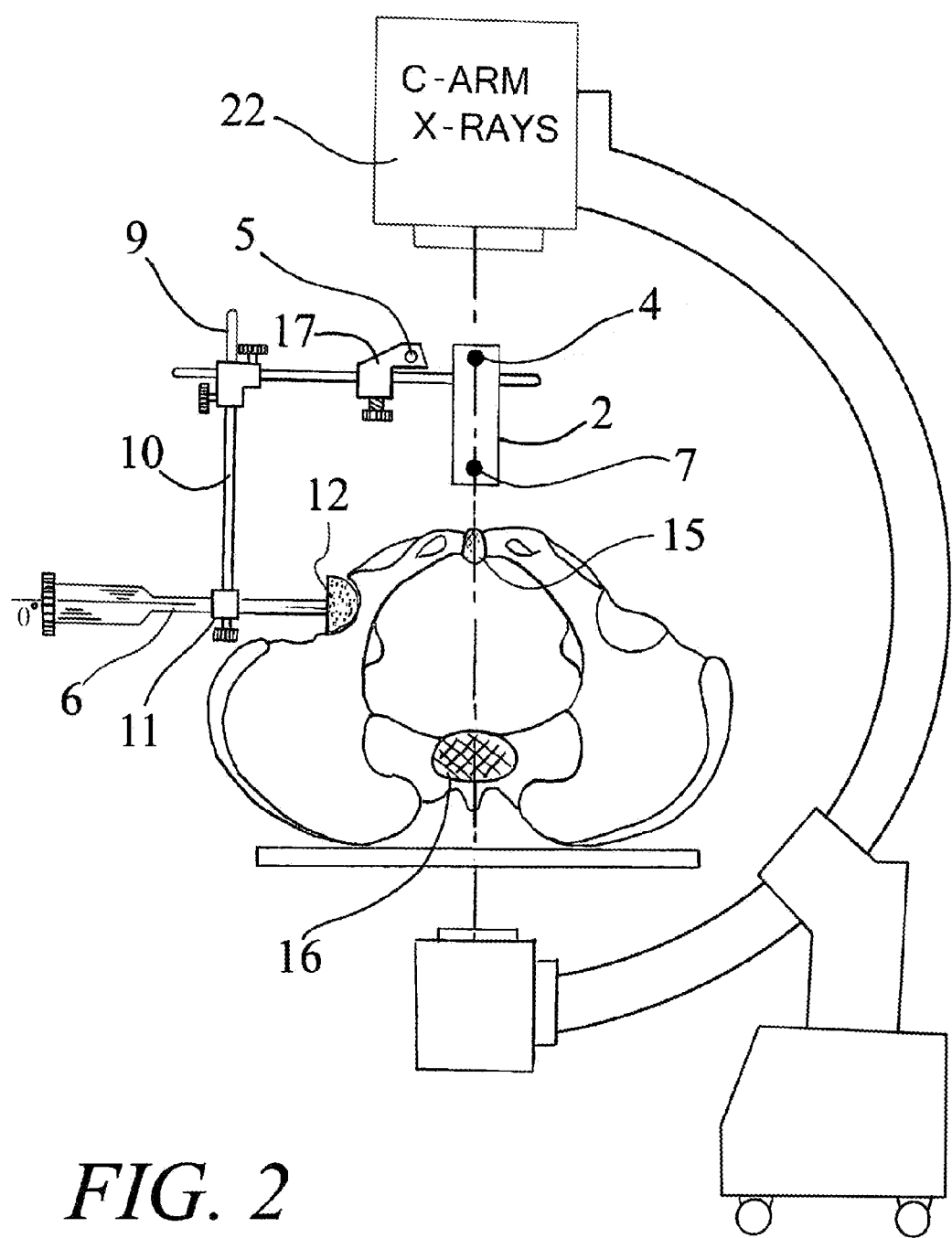
FIG. 2 is a perspective side view of the cup positioning device inserted in the acetabular cavity in neutral position (zero anteversion).
Figure 3:
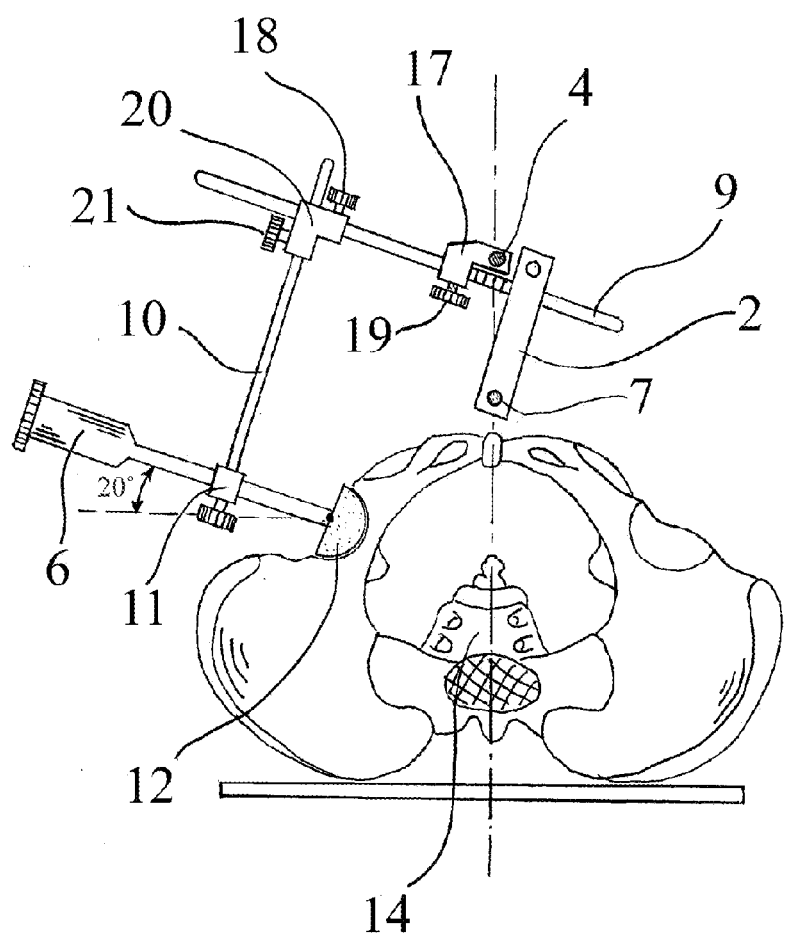
FIG. 3 is a perspective side view of the cup positioning device inserted in the acetabular cavity in 20 degrees of anteversion.

Turning now descriptively to the drawings, in which similar references characters denote similar elements throughout the several views, the attached figures illustrate the acetabular cup positioning device, which comprises two metallic horizontal and vertical shafts 9 and 10 perpendicular to each other and a firmly connected by a faster 20 having two separate knobs 18 and 21 for holding the vertical and horizontal rods in locked position. Furthermore, said vertical shaft 10 is firmly attached to the acetabular cup inserter 6 via fastener 18. The end of impactor 6 will receive the acetabular cup implant 12 that will be impacted into the acetabular cavity prepared by the surgeon in the pelvic bone as seen in FIGS. 2, 3, and 4.

Figure 4:
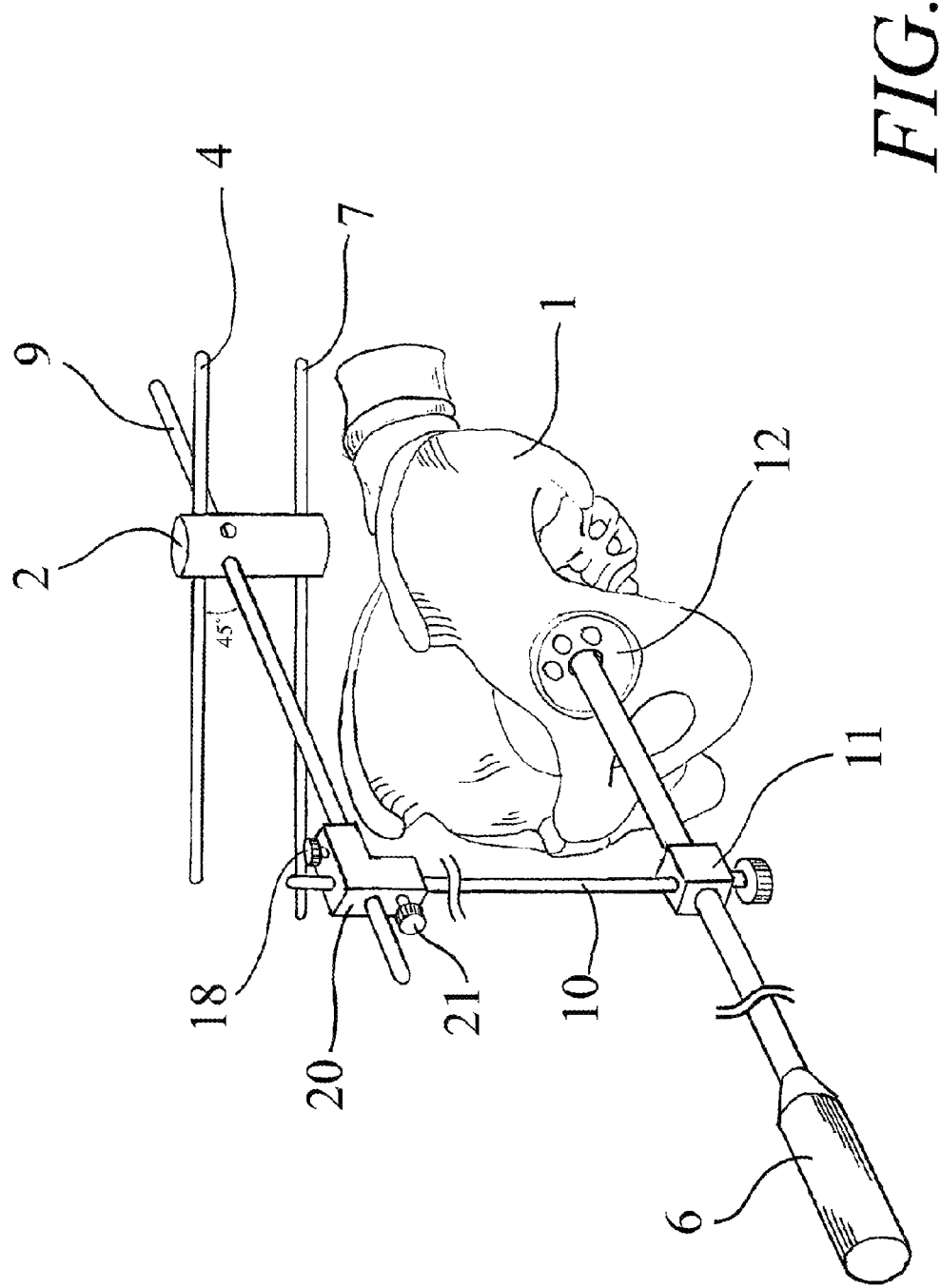
FIG. 4 is a perspective view of the cup positioning device inserted in the acetabular cavity in neutral position.
Figure 5:
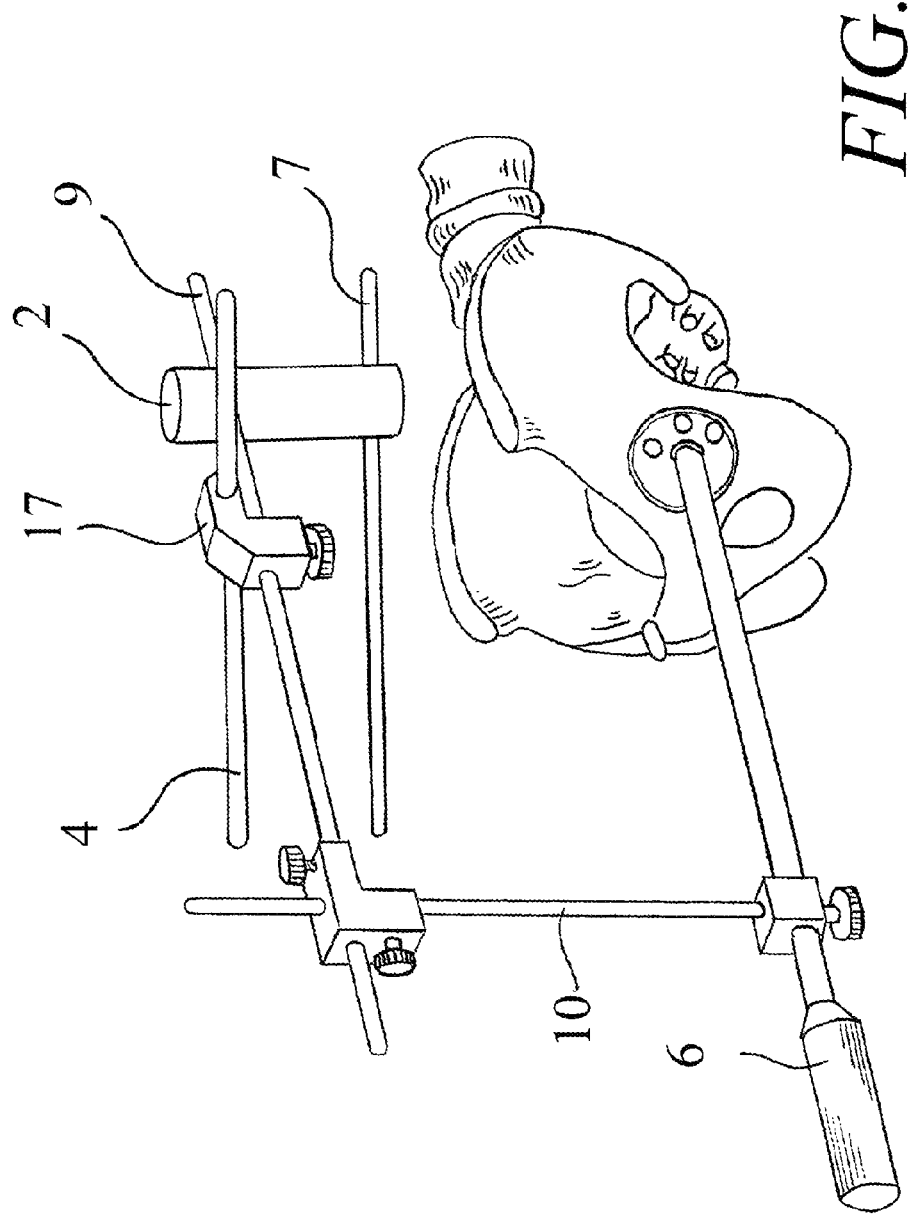
FIG. 5 is a perspective view of the cup positioning device inserted into the acetabular cavity in anteversion using the anteversion rod.

The horizontal metallic shaft 9 is slidingly attached to fastener 20 at one end and has on the other end two horizontal inclination rods 4 and 7 situated in a parallel fashion and superimposed as seen in FIG. 4. Said parallel and horizontal rods are being connected by vertical central cylinder 2. Furthermore, the angle between the horizontal shaft 9 and inclination rods 4 and 7 is 45 degree angle which is the correct angle for inclination (See FIG. 4). The anteversion bracket 17 is slidably situated onto horizontal shaft 9 having a channel 5 situated at 45 degrees angel with said horizontal shaft 9.

More descriptively, the acetabular cup being held by the orientation device is placed by the surgeon into the acetabular cavity. Fluoroscopy x-ray C arm 22 is used to align the two parallel horizontal bars 4 and 7 along the center of the first sacral vertebrae and the center of the symphysis pubis readily seen on the fluoroscopy screen. In doing so, the angle between the impactor 6 and the two parallel horizontal bars 4 and 7 being 45 degrees will automatically make the angle of inclination of the cup inserter 45 degrees. In other words, aligning the two parallel horizontal rods with the central midline anatomy as described above, will place the impactor handle at 45 degrees inclination and neutral anteversion or level with pelvis. The surgeon then has to determine the anteversion angle of the cup.

The surgeon will remove the upper inclination rod 4 from the vertical central cylinder 2 and insert it in the oblique channel 5 of the anteversion bracket 17. In addition, a plurality of markings in a form of sliding scale 23 located on the central portion of shaft 9 are used to determine the degrees of anteversion. The surgeon will slide bracket 17 to that number and locks it by tightening knob 19. The surgeon will then rotate the inserter 6 of the impactor so that anteversion bar 4 and lower horizontal inclination bar 7 are superimposed under X-ray image and appear as one. During anteversion, the surgeon may have to release knob 18 and slide back rod 9 in order to bring rod 7 and 4 back to the midline (see FIG. 3).

It is to be understood that the above description is intended to be illustrative and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. For example, some or all of the shafts and/or rods can be made out of ceramic, radiopaque plastic or metallic alloy. Therefore, the scope of the invention should be, therefore, determined with reference to the appended claims, along with the full scope of equivalents to which such claims are entitled.

What is claimed:

1. An orthopedic surgical device for positioning an acetabular cup implant in a surgically prepared acetabular cavity comprising: a primary vertical shaft and an acetabular cup inserter shaft, said primary vertical shaft being perpendicularly coupled to said acetabular cup inserter shaft; a secondary shaft perpendicularly coupled to said primary vertical shaft via a sliding locking bracket; an upper alignment rod horizontally secured to said secondary shaft via a vertical central cylinder; a lower alignment rod secured parallel and horizontal to said upper alignment rod through said vertical central cylinder; and an anteversion bracket having a channel able to receive anteversion rod, arranged approximately 45 degrees to said secondary shaft, wherein said anteversion bracket is slidably attached to said secondary shaft, wherein under fluoroscopy when said upper alignment rod and said lower alignment rod are parallel, horizontally aligned and superimposed on midline of an anatomical bony pelvic landmark, the acetabular cup inserter shaft is automatically aligned at 45 degrees of inclination to said midline, and wherein at a predetermined anteversion and under fluoroscopy, the anteversion rod is aligned with the lower alignment rod and superimposed on the midline of an anatomical bony pelvic landmark.

2. The orthopedic surgical device of claim 1, wherein said rods or shafts are made from either ceramic, radiopaque plastic, or metallic alloy.

3. The orthopedic surgical device of claim 2, wherein said vertical central cylinder allows the secondary shaft to be used wherein the approximate 45 degree angle can be either to the right or left.

4. The orthopedic surgical device of claim 2, wherein said upper alignment rod and said lower alignment rod are parallel-superimposed for use with a portable fluoroscopy C-arm unit.

5. The orthopedic surgical device of claim 4, wherein x-ray shadows are formed by said upper and lower alignment rods for superimposing on the midline of an anatomical bony pelvic landmark.

6. The orthopedic surgical device of claim 5, wherein when said upper and lower alignment rods are parallel and horizontally aligned, the acetabular cup inserter shaft is automatically aligned at 45 degrees of inclination to said midline.

7. The orthopedic surgical device of claim 1, wherein the angle between the secondary shaft and any alignment rod is approximately 45 degrees.

8. The orthopedic surgical device of claim 1, wherein the central portion of said secondary shaft further comprises a numeric scale in degrees that correspond to the degrees of anteversion.

* * * * *